United States Patent [19]
Martin

[11] Patent Number: 6,015,836
[45] Date of Patent: Jan. 18, 2000

[54] CHEMICAL DISINFECTANT EMPLOYING DUAL CHAIN QUATERNARY AMMONIUM COMPOUNDS WITH IODINE

[76] Inventor: Howard Martin, 11500 W. Hill Dr., Rockville, Md. 20852

[21] Appl. No.: 09/179,795

[22] Filed: Oct. 27, 1998

Related U.S. Application Data

[60] Provisional application No. 60/063,429, Oct. 28, 1997.

[51] Int. Cl.[7] .......................... A61K 33/18; A61K 31/14
[52] U.S. Cl. .......................... 514/642; 514/642; 514/728; 514/731; 514/5; 424/51; 424/78.07; 424/667; 424/672
[58] Field of Search ................ 514/23, 643, 642, 514/724; 424/80; 252/8.8, 542, 8.6; 427/2

[56] References Cited

U.S. PATENT DOCUMENTS

| | | | |
|---|---|---|---|
| 4,220,562 | 9/1980 | Spadini et al. | 252/542 |
| 4,321,257 | 3/1982 | Sipos | 424/80 |
| 4,783,340 | 11/1988 | Mcdonell et al. | 427/2 |
| 5,232,914 | 8/1993 | Fellman | 514/23 |
| 5,284,875 | 2/1994 | Martin | 514/643 |
| 5,510,042 | 4/1996 | Hartman et al. | 252/8.8 |

*Primary Examiner*—Keith D. MacMillan
*Assistant Examiner*—Vickie Kim
*Attorney, Agent, or Firm*—Law Offices of Royal W. Craig

[57] ABSTRACT

A new and improved formulation of a dual chain quaternary ammonium chloride compound and iodine/potassium iodide complex to serve as a disinfectant and sanitizer on surfaces and tissue as well as being utilized as an immersion solution in health care areas. The dual-quat with iodine formulation of the present invention is more useful over a wide range of areas and uses and is also more stable over a wide variety of water combinations. It improves efficacy, reduces toxicity, increases the spectrum of the antimicrobial effectiveness and broadens the effective usage of the complex into new areas of application.

13 Claims, 4 Drawing Sheets

FIG. 1

TABLE 1

KWIKKILL-IODINE (KK-I) READY TO USE

Results of the AOAC Use Dilution Screens Test, using *Staphylococcus aureus*, *Salmonella choleraesuis* & *Pseudomonas aeruginosa*, when tested at 20° +/-1° C

| Test Organism | Contact Time | # Positive /Total Tubes |
| --- | --- | --- |
| Staphylococcus aureus | 1 minute | 0/5 |
| Salmonella choleraesuis | 1 minute | 0/5 |
| Pseudomonas aeruginosa | 3 minutes | 1/5 |
| Pseudomonas aeruginosa | 4 minutes | 0/10 |
| Escherichia coli | 1 minute | 0/5 |
| Streptococcus pyogenes | 1 minute | 0/5 |

Note: All bacterial back counts were between $2 \times 10^6$ and $7 \times 10^7$ / carrier.

FIG. 2

TABLE 2

KWIKKILL-IODINE (KK-I) READY TO USE

Results of AOAC Fungicidal Tests, using *Trichophyton mentagrophytes*, when tested at 20° C +/-1° C

| Test Organism | Contact Time | # Positive / Total Tubes |
| --- | --- | --- |
| Trichophyton mentagrophytes | 3 minutes | 0/20 |

Note: # reported fungal conidia = $7.8 \times 10^5$ / carrier.

FIG. 3

TABLE 3

KWIKKILL-IODINE (KK-I) READY TO USE

Results of AOAC Tuberculocidal Test, using *Mycobacterium bovis* (BCG), when tested at 20° C +/-1° C

| Test Organism | Contact Time | # Positive / Total Tubes |
| --- | --- | --- |
| Mycobacterium bovis (BCG) | 10 minutes | 0/60 |
| Mycobacterium bovis (BCG) | 10 minutes | 0/30 |

TABLE 4

KWIKKILL-IODINE (KK-I) READY TO USE

Results of Virucidal Tests, using listed Viruses, when tested at 22° C +/-1° C

| Test Organism | Contact Time* | Killed at least 4 logs of virus |
|---|---|---|
| HIV (AIDS virus) | 2 minutes | yes |
| Herpes Simplex Virus 2 | 2 minutes | yes |
| Influenza $A_2$HK | 2 minutes | yes |
| Influenza $A_2$ Japan | 5 minutes | yes |
| Poliovirus 2 | 5 minutes | yes |
| Adenovirus Type 5 | 5 minutes | yes |
| Vaccinia virus | 5 minutes | yes |
| Avian influenza A/ Turkey/Wisconsin | 5 minutes | yes |

* Contact times for virucidal testing was choosen to minimize the needs for repeat testing and to fall within the maximum limit of 10 minutes. Times were based on the previous experience of the testing laboratory with similar product types.

TABLE 5

KWIKKILL-IODINE (KK-I) READY TO USE

Results of Tests against various Oilfield and CoolingTower Test Organisms, when tested at 20° C +/-1° C

| Test Organism | Contact Time* | Killed at least 6 logs of test organism |
|---|---|---|
| Organisms found in oil wells | | |
| Desulfovibrio desulfuricans | 5 minutes | yes |
| Pseudomonas aeruginosa | 5 minutes | yes |
| Pseudomonas fluorscens | 5 minutes | yes |
| Organisms found in cooling towers | | |
| Bacteria | | |
| Pseudomonas aeruginosa | 3 minutes | yes |
| Pseudomonas fluorscens | 3 minutes | yes |
| Escherichia coli | 3 minutes | yes |
| Candida albicans | 1 minute | yes |
| Streptococcus pyogenes | 20 seconds | yes |

| Algae | | Killed at least 4 logs of test organism |
|---|---|---|
| Green Algae | 5 minutes | yes |
| Blue-Green Algae | 5 minutes | yes |

TABLE 6

KWIKKILL-IODINE (KK-I) READY TO USE

Results of Tests against Staphylococcus aureus, and Enterobacter aerogenes, using the EPA Non Food Use Sanitizer Procedure, when tested at 20° C +/-1° C, with a 5 minute contact time.

| Test Organism | Carrier Type | # Test Organisms Killed |
|---|---|---|
| Staphylococcus aureus | Stainless steel | $5.8 \times 10^6$ |
| Staphylococcus aureus | Glass | $3.7 \times 10^6$ |
| Enterococcus aerogenes | Stainless steel | $6.0 \times 10^6$ |
| Enterococcus aerogenes | Glass | $4.5 \times 10^6$ |

FIG. 6

TABLE 7

LEGIONELLA TEST

METHOD: Logarithmic reduction as per EPA(DIS/TSS)TB.1986

GROWTH MEDIUM: CYE Enrichment Agar

SUBCULTURE MEDIUM: CYE Enrichment Agar

EXPOSURE TIME: 0, 5, 10, 15, 20 Minutes

EXPOSURE TEMP: Start 23 C End 23 C

NEUTRALIZER TIME: 10 minutes @ 23 C

INCUBATION: 2 days @ 37 C

NEUTRALIZER: Letheen Broth with Tween 80

RESULTS:

KWIKKILL, A FORTIFIED QUATERNARY AMMONIUM CHLORIDE FORMULATION, DILUTED 1 OZ. TO THE GALLON (1:128) COMPLETELY INACTIVATED LEGIONELLA PNEUMOPHILIA IN 10 MINUTES AT A CONCENTRATION OF 1,560 PPM TOTAL QUATERNARY AMMONIUM CHLORIDE. AT A CONCENTRATION OF 100 PPM, 20 MINUTES EXPOSURE AT 23 C WAS REQUIRED FOR TOTAL INACTIVATION.

*FIG. 7*

CHEMICAL DISINFECTANT EMPLOYING DUAL CHAIN QUATERNARY AMMONIUM COMPOUNDS WITH IODINE

CROSS-REFERENCE TO RELATED APPLICATIONS

The present application is based on U.S. provisional application Ser. No. 60/063,429 filed on Oct. 28, 1997.

BACKGROUND OF THE INVENTION

1. Field of the Invention

The present invention relates to chemical disinfection and sanitizing and, more particularly, to the use of quaternary ammonium compounds and iodine for the same.

2. Description of the Background

The purpose of disinfection is to reduce microbial contamination to such a level that an infective dose is not liable or capable of reaching a susceptible site or patient. Presently there are several combinations of quaternary ammonium compounds that can accomplish this within strict limitations based upon their physical chemistries. However, the existing combinations cannot achieve this task in all types of situations. For example, these existing formulations are limited based upon their dilution with hard water, that is water with more than 400 ppm of carbonates in it. This is because quaternary ammonium compounds are inactivated by hard water. Quaternary ammonium compounds are inhibitory to vegetative organisms and fungii but are not tuberculocidal or sporicidal. Dual quat formulations have improved biocidal activity, stronger detergency and a low level of toxicity however they have not solved the the environmental problem of hard water and proteinaceous soilage that reduces or inhibits their activity. What is required was a solution to reduce the hard water problem and improve the biocidal activity while still maintaining a low level of toxicity.

U.S. Pat. No. 4,983,635 issued Jan. 8, 1991, and U.S. Pat. No. 5,284,875 issued Feb. 8, 1994, solved the hard water problem and improved but did not effectively solve the biocidal activity, and due to the phenolics increased the toxicity problem.

Iodine is one of the most effective antimicrobial agents known. It is essentially bactericidal, dilutions possessing bacteriostatic and bactericidal action being practically identical. Iodine is active against a broad series of organisms including TB, pathogenic fungii, viruses of both lipophilic and hydrophilic types. Although effective as an antiseptic wash and irrigant over a wide pH range it is best at an acid pH.

It would be greatly advantageous to provide a non-toxic iodine constituent as an effective antimicrobial agent in a dual-quat formulation.

SUMMARY OF THE INVENTION

It is, therefore, an object of the present invention to provide a new formulation of quaternary ammonium compound that is more useful over a wide range of areas and uses and is also more stable over a wide variety of water combinations.

It is another object to include iodine as a biocide with the quaternary ammonium compound. Iodine has a low toxicity component, and is applicable on all hard surfaces including a tissue or a food surface, and as an inhalant.

It is another object to provide a formulation of dual quaternary ammonium compound and iodine which comes together to solve and improve the efficacy, reduce toxicity, increase the spectrum of the antimicrobial effectiveness and broaden the effective usage of the dual quaternary ammonium/iodine complex into new areas of application.

In accordance with the above-described and other objects, the present invention provides a new and improved formulation of a dual chain quaternary ammonium chloride compound and iodine/potassium iodide complex to serve as a disinfectant and sanitizer on surfaces and tissue as well as being utilized as an immersion solution in health care areas.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 1 is a table showing the results of AOAC dilution screen tests using Staphylococcus aureus, Salmonella choleraesuis, and Pseudomonas aeruginosa, when tested at 20 degrees C. using dual chain quaternary ammonium compounds with iodine as in the present invention.

FIG. 2 is a table showing the results of AOAC Fungicidal Tests, using Trichophyton mentagrophytes, when tested at 20 degrees C.

FIG. 3 is a table showing the results of AOAC Tuberculocidal Test, using Mycobacterium bovis (BCG), when tested at 20 degrees C.

FIG. 4 is a table showing the results of AOAC Tuberculocidal Test, using Mycobacterium bovis (BCG), when tested at 20 degrees C.

FIG. 5 is a table showing the results of tests against various Olifield and CoolingTower test organisms when tested at 20 C.

FIG. 6 is a table showing the results of tests against staphylococcus aureus, and enterobacteraero genes, using the EPA non food use sanitizer procedure, when tested at 200 C, with a 5 minute contact time.

FIG. 7 is a table showing the results of a Legionella test under the specified conditions.

DETAILED DESCRIPTION OF THE PREFERRED EMBODIMENTS

A significant improvement in disinfection and sanitizing has been developed by the use of quaternary ammonium compounds and iodine, developed as a synergistic combination that is superior to the present ordinary quaternary formulations that utilize alcohols or phenols. The reduction of microbial contamination to such a level that an infective dose is not liable or capable of reaching a susceptible site or patient is the purpose of disinfection. Presently there are several combinations of quaternary ammonium compounds that can accomplish this within strict limitations based upon their physical chemistries. However, the purpose of this newly developed formulation is to be able to accomplish this task in all types of situations making the formulation more useful for the general public health and therefore more economical as well. The formulation of the present invention creates, in essence, a new compound that is more useful over a wide range of areas and uses and is also more stable over a wide variety of water combinations.

The formulation of the present invention is specifically blended to come together to solve and improve the efficacy, reduce toxicity, increase the spectrum of the antimicrobial effectiveness and broaden the effective usage of this specific dual quaternary ammonium/iodine complex into new areas based upon this new formulation.

It is with the inclusion of iodine as a biocide, which has a low toxicity component, and is applicable on all hard surfaces including a tissue or a food surface, and as an inhalant that a new and significantly improved formulation has been tested and developed.

As described above, Iodine is one of the most effective antimicrobial agents known (as antiseptic wash and irrigant over a wide pH range). It can be used as a skin degermer even at an concentration of 2% without adverse effect. It has a low surface tension especially when combined with alcohol which dissolves skin oils and facilitates penetration into the epidermal layer thus destroying both the transient and resident bacterial flora. A 2 minute hand scrub test showed that a 1% iodine and 70% ethyl alcohol formulation reduced skin flora by 80% which was equivalent to a 13 minute brush and soap scrub.

Iodine is less affected by organic matter than the dual chain quats or phenolics. If the free iodine available is at least 50–75 ppm there will be a rapid germicidal action. Complexed iodine is a slow release compound and therefore limits its toxicity. It has been shown that iodine activity is greater at a low pH than at an alkaline pH. This formulation is purposefully kept acidic for both the activity of the dual, chain quat and the iodine. The effective method of antimicrobial action is the development of the "H" pattern for which it has a high affinity when the solute is almost completely adsorbed. This was demonstrated by ionic exchange in yeast studies conducted by Hugo and Newton "The Adsorption of Iodine from Solution by Microorganisms and by Serum, *J Pharm & Pharmacology,* 16:48–55, (1964).

The iodine itself is complexed with potassium iodide to act as a solubilizing agent. Alcohol solutions will enhance the effect of the iodine activity and that is one of the functions of the isopropyl/ethyl alcohol portion of the formulation.

The dual chain quat acts as a carrier as well as acting for itself as an added biocide and detergent. The active iodine is released depending on the vehicle in which it is dissolved and therefore it has more availability to the site. The ability of the dual chain quat to act as a surface tension reducer, wetting agent and dispersing agent enables the iodine complex formulation to become more effective as an antimicrobial formula than the individual components, a synergistic effect. The iodine component is enhanced by this complexing with the quat. The undesirable iodine properties of corrosiveness, as in Wescodyne, irritation and poor solubility are now overcome when complexed with the dual chain quats, alcohol and acidic formulation.

The dual chain quat is not equally effective against all organisms as is iodine. Gram negative organisms are more resistant to the pure quat formulation, especially pseudomonas, than gram positive bacteria. The iodine component of the new formulation eliminates this problem. This is shown by the ability of the iodine to adsorb and penetrate the gram negative cell wall which the quats alone can not achieve. It is this significant combination that allows the new improved Martin formulation to be significantly improved over the previous one and to enable this formulation to have a more effective and wider spectrum of antimicrobial activity. The quat works as an anitimicrobial agent due to its physical properties more so than its chemical properties which is a different chemistry from the iodine component. The two components together create a physical-chemical cidal effectiveness superior to the other formulations. A critical and important difference between iodine and the quat phenol previous combination is the reactions with organic material. It was shown, in peptone solutions, that iodine reacts very slowly with proteins. In disinfection under conditions occurring in practice, i.e. in the presence of blood, serum, or any dissolved proteinaceous material, iodine is more efficient because the iodine concentration available for actual disinfection is greater. The low reactivity with proteins is a key improvement and difference in the new formulation versus the quat/phenolic which has an affinity for organic material.

The stability of iodine solutions has been brought into question. It was determined that keeping the pH acidic, 6 or below, there was no formation of the iodate complex which causes dissolution of the disinfecting component. Therefore the new formulation has solved the iodine stability problem.

The problem of the dual phenolics in prior formulations by the inventor herein (U.S. Pat. No. 4,983,635 issued Jan. 8, 1991, and U.S. Pat. No. 5,284,875 issued Feb. 8, 1994) has been significantly improved upon by the chemical addition and chemical adjustments to incorporate iodine as a replacement active ingredient. What has been developed is a new and improved formulation that gives a faster biocidal kill, can be utilized on food surface areas where the quat/phenolic can not, is less toxic than phenolics and quats, is non sensitizing, less irritating as it can be used on mucous membranes or skin, is non staining versus the usual iodine compounds, has a broader spectrum of kill than the quat/phenolic, the pH is near neutral, works at less than room temperature, that is at 20 C or 68 F, it is environmentally safer than the phenolics and can be disposed of directly without neutralizers as is EPA required for phenols. It is a more stable product than any of the individual components of the formulation exhibiting a two year shelf life.

The addition of the nonylphenol is as a wetting agent so the formulation may be utilized in pre soaked or moistened wipes for surface or skin disinfection. The formula may also be used as an immersion solution to disinfect and clean, as well as a prepared spray solution. The formula being non toxic can be used as a sanitizer, or disinfection solution in either a wipe, spray or immersion soak on food surface areas, counter tops etc. It also can be utilized as a non terminal disinfectant on medical/dental instruments. It has been tested in cooling towers and will kill legionella in 20 minutes and has been approved for cooling towers usage by the US EPA (See FIG. 7).

The tables shown in FIGS. 1–7 indicate the improved testing time of the dual chain quaternary ammonium compounds/iodine of the present invention (designated KK-I).

FIG. 1 is a table showing the results of AOAC dilution screen tests using Staphylococcus aureus, Salmonella choleraesuis, and Pseudomonas aeruginosa, when tested at 20 degrees C. using dual chain quaternary ammonium compounds with iodine as in the present invention.

FIG. 2 is a table showing the results of AOAC Fungicidal Tests, using Trichophyton mentagrophytes, when tested at 20 degrees C.

FIG. 3 is a table showing the results of AOAC Tuberculocidal Test, using Mycobacterium bovis (BCG), when tested at 20 degrees C.

FIG. 4 is a table showing the results of AOAC Tuberculocidal Test, using Mycobacterium bovis (BCG), when tested at 20 degrees C.

FIG. 5 is a table showing the results of tests against various Olifield and CoolingTower test organisms, when tested at 20 degrees C.

FIG. 6 is a table showing the results of tests against staphylococcus aureus, and enterobacter aero genes, using the EPA non food use sanitizer procedure, when tested at 20 degrees C, with a 5 minute contact time.

FIG. 7 is a table showing the results of a Legionella test under the specified conditions.

Having fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

What is claimed is:

1. A composition for disinfecting and sanitizing surfaces and for de-germing of skin, comprising the following in combination:

a dual chain quaternary ammonium compound;

iodine of at least 50 ppm for rapid germicidal action;

potassium iodide complexed with said iodine to act as a solubilizing agent;

alcohol to enhance the rapid germicidal action of the iodine;

ethoxylated nonylphenol; and deionized water;

whereby said composition has an acidic pH level to improve stability.

2. The composition for disinfecting and sanitizing surfaces and for de-germing of skin according to claim 1, wherein said dual chain quaternary ammonium compound further comprises N-alkyl dimethylethylbenzyl ammonium chloride.

3. The composition for disinfecting and sanitizing surfaces and for de-germing of skin according to claim 1, wherein said dual chain quaternary ammonium compound further comprises N-alkyl dimethylbenzyl ammonium chloride.

4. The composition for disinfecting and sanitizing surfaces and for de-germing of skin according to claim 1, wherein a concentration of said dual chain quaternary ammonium compound relative to other constituents is approximately 0.4%+/−0.05%.

5. The composition for disinfecting and sanitizing surfaces and for de-germing of skin according to claim 1, wherein a concentration of said iodine relative to other constituents is approximately 0.024%+/−0.003%.

6. The composition for disinfecting and sanitizing surfaces and for de-germing of skin according to claim 1, wherein a concentration of said potassium iodide relative to other constituents is approximately 0.017%+/−0.002%.

7. The composition for disinfecting and sanitizing surfaces and for de-germing of skin according to claim 1, wherein a concentration of said alcohol relative to other constituents is approximately 22%+/−2.2%.

8. The composition for disinfecting and sanitizing surfaces and for de-germing of skin according to claim 1, wherein a concentration of said ethoxylated nonylphenol relative to other constituents is approximately 0.2%+/−0.02%.

9. The composition for disinfecting and sanitizing surfaces and for de-germing of skin according to claim 1, wherein a concentration of said deionized water relative to other constituents is approximately 77.4%+/−0.8%.

10. The composition for disinfecting and sanitizing surfaces and for de-germing of skin according to claim 1, wherein said alcohol further comprises isopropyl alcohol.

11. The composition for disinfecting and sanitizing surfaces and for de-germing of skin according to claim 1, wherein said alcohol further comprises ethyl alcohol.

12. The composition for disinfecting and sanitizing surfaces and for de-germing of skin according to claim 1, wherein said iodine is complexed with said potassium iodide to act as a solubilizing agent.

13. The composition for disinfecting and sanitizing surfaces and for de-germing of skin according to claim 1, wherein said alcohol is a catalyst for a biocidal activity of said iodine.

* * * * *